(12) United States Patent
Maurer et al.

(10) Patent No.: US 11,073,462 B2
(45) Date of Patent: Jul. 27, 2021

(54) NON-ACTIVATED PLATELET TRANSFUSION METHODS FOR ENHANCEMENT OF PATIENT TREATMENT OUTCOMES

(71) Applicant: Lightintegra Technology Inc., Vancouver (CA)

(72) Inventors: Elisabeth Maurer, Vancouver (CA); Daniel Millar, Vancouver (CA)

(73) Assignee: LightIntegra Technology Inc., Vancouver (CA)

( * ) Notice: Subject to any disclaimer, the term of this patent is extended or adjusted under 35 U.S.C. 154(b) by 185 days.

(21) Appl. No.: 16/209,387

(22) Filed: Dec. 4, 2018

(65) Prior Publication Data
US 2019/0204202 A1   Jul. 4, 2019

Related U.S. Application Data

(60) Provisional application No. 62/595,221, filed on Dec. 6, 2017.

(51) Int. Cl.
*G01N 15/06* (2006.01)
*A61K 35/19* (2015.01)
(Continued)

(52) U.S. Cl.
CPC .......... *G01N 15/06* (2013.01); *A61K 35/19* (2013.01); *G01N 33/49* (2013.01);
(Continued)

(58) Field of Classification Search
CPC ........ G01N 15/06; G01N 15/00; G01N 33/49; G01N 33/487; G01N 33/483; G01N 33/48; A61K 35/19; A61K 35/14; A61K 35/12
(Continued)

(56) References Cited

U.S. PATENT DOCUMENTS 6,025,201 A * 2/2000 Zelmanovic ....... G01N 15/1459
356/336
7,341,873 B2   3/2008 Maurer-Spurej
(Continued)

FOREIGN PATENT DOCUMENTS

| EP | 90100371.5 | 7/1990 |
|---|---|---|
| WO | 2013003112 | 1/2013 |
| WO | 2018053010 | 3/2018 |

OTHER PUBLICATIONS

Maurer-Spurej, Elisabeth, et al, Platelet quality measured with dynamic light scattering correlates with transfusion outcome in hematologic malignancies, Transfusion, Nov. 2009, vol. 49, p. 2276-2284. (Year: 2009).*
(Continued)

*Primary Examiner* — Christine T Mui
(74) *Attorney, Agent, or Firm* — Hancock Hughey LLP (57) ABSTRACT

To reduce the complexity and risk associated with activated platelet transfusions, thrombocytopenic patients are transfused with exclusively non-activated platelets. A preferred embodiment is through routine screening of platelet units in the hospital blood bank using dynamic light scattering and selective allocation of platelets, with non-activated platelets being exclusively transfused to thrombocytopenic patients, especially patients with cancers such as hematologic malignancies. Activated platelets typically contain activated factors of the innate immune system called complement, transforming growth factor beta (TGFβ), interleukin 6 (IL-6), CD40 ligand (CD40L) and C-reactive protein (CRP) for example. Some of these activated factors have already been shown to correlate with microparticles and others are expected to correlate: the higher the platelet activation the more microparticles and the higher the concentration of
(Continued)

these factors. By transfusing only non-activated platelets, therapeutic outcomes are enhanced.

20 Claims, 5 Drawing Sheets

(51) Int. Cl.
    *G01N 33/49*         (2006.01)
    *G01N 15/00*         (2006.01)

(52) U.S. Cl.
    CPC ........... *G01N 2015/0053* (2013.01); *G01N 2015/0084* (2013.01); *G01N 2015/0693* (2013.01)

(58) Field of Classification Search
    USPC .......................................... 436/63
    See application file for complete search history.

(56) References Cited

U.S. PATENT DOCUMENTS

| | | |
|---|---|---|
| 8,323,922 B2 | 12/2012 | Maurer et al. |
| 8,834,129 B2 | 9/2014 | Barnes |
| 9,500,655 B2 | 11/2016 | Fantl et al. |
| 9,939,436 B2 | 4/2018 | Basabe-Desmonts et al. |
| 2011/0263452 A1 | 10/2011 | Basabe-Desmonts et al. |
| 2013/0130279 A1 | 5/2013 | Fantl et al. |
| 2016/0231338 A1 | 8/2016 | Aster |
| 2017/0153256 A1 | 6/2017 | Bohm et al. |
| 2017/0218339 A1 | 8/2017 | Balduini et al. |

OTHER PUBLICATIONS

ABELA, Laser-light scattering, a new method for continuous monitoring of platelet activation in circulating fluid, 2003, J Lab Clin Med, vol. 141, No. 1, p. 50-57. (Year: 2003).*

Elisabeth Maurer-Spurej et al., Portable dynamic light scattering instrument and method for the measurement of blood platelet suspensions, 2006 Phys. Med. Biol. 51 3747 (Year: 2006).*

Maurer-Spurej et al., Microparticle Content of platelet concentrates is predicted by donor microparticles and is altered by production methods and stress; Transfusion and Apheresis Science; 55 (2016) 35-43.

Warkentin, Platelet Microparticle Generation Assay for Detection of HIT Antibodies: Advance, Retreat, or Too Soon to Tell?; Thrombosis Research; 133 (2014) 957-958.

Mullier et al., Platelet microparticle generation assay: A valuable test for immune heparin-induced thrombocytopenia diagnosis; Thrombosis Research; 133 (2014) 1068-1073; online Dec. 9, 2013.

US Patent Office action dated Feb. 5, 2021 from U.S. Appl. No. 16/269,668, assigned to the assignee of the present application.

Xu, Yan, Nobu Nakane, and Elisabeth Maurer-Spurej. "Novel test for microparticles in platelet-rich plasma and platelet concentrates using dynamic light scattering." Transfusion 51.2 (2011): 363-370. (Year: 2011).

Rauova, Lubica, et al. "Ultralarge complexes of PF4 and heparin are central to the pathogenesis of heparin-induced thrombocytopenia." Blood 105.1 (2005): 131-138. (Year: 2005).

* cited by examiner

NON-ACTIVATED PLATELET TRANSFUSION METHODS FOR ENHANCEMENT OF PATIENT TREATMENT OUTCOMES

TECHNICAL FIELD

The present invention relates to the field of treatment of patients with thrombocytopenia for example due to cancer, and more particularly to methods of enhancing treatment outcomes for such patients especially including hematology-oncology patients through the transfusion of non-activated platelets.

BACKGROUND OF THE INVENTION

Most oncologists consider platelet transfusions as supportive treatment mostly to treat the side effect of low platelet count (thrombocytopenia) and avoid bleeding. This prophylactic use of platelets to increase platelet count is mostly for blood cancer patients but also other cancers and conditions especially when the platelet count decreases due to very aggressive treatment.

Oncologists may assume that the platelets in platelet transfusions are non-activated but—as is known in the art—this is not the case: Potentially 50% of platelet transfusions contain activated platelets and it is known that activated platelets could harm the patient.

The activation of platelets is a well-documented phenomenon. It is clear that a large percentage of donated platelet units contain activated platelets. This situation can lead to serious implications for the treatment of hematology-oncology patients who are dependent on platelet transfusion support during their treatment.

Activated Platelets

Platelet activation refers to the transition from the resting discoid platelets to dendritic spheres. This phenomenon occurs in response to a stressor, but not necessarily as part of the clotting cascade. It is becoming clear that the primary source for activated platelets in a platelet unit is the donor. The donor's immunological and inflammatory state at the time of donation appears to influence the activation status of their platelets. These donor factors are often asymptomatic and are not caught in donor screening, meaning a surprisingly high number of activated platelets are transfused. The rate of activated platelet products in hospitals ranges between 30% and 50% of the platelet inventory. Activation rates falling in this range have been observed across North America and Europe.

Activated Platelets and Refractoriness

Transfusions with activated platelets tend to result in lower count increments. Hospitals that transfused primarily non-activated platelets to their hematology-oncology patient populations have seen drastic reductions in the rate of patients requiring massive transfusion support, and the average number of transfusions per patient. These observations have been attributed to interactions between activated platelets and the recipient's innate immune system. In particular complement opsonization may be the cause of many otherwise unexplained occurrences of platelet refractoriness.

Activated Platelets and Immunotherapy

In addition to the implications of activated platelets on platelet refractoriness, a growing body of literature is suggesting activated platelets may interfere with certain immunotherapies. It has been shown that activated platelets contain various upregulated factors that suggest platelets may be a highly immunomodulatory treatment. Specifically TGFβ, IL-6, CD40L and complement are found in conjunction with activated platelets. This serves to add complexity to the treatment of already very complex patients.

Thus, activated platelets in platelet transfusion products most likely also contain important chemicals such as activated factors of the innate immune system called complement, transforming growth factor beta (TGFβ), interleukin 6 (IL-6), CD40 ligand (CD40L) and C-reactive protein (CRP) to mention just a few. Some of these factors have already been shown to correlate with microparticles and others are expected to correlate: the higher the platelet activation the more microparticles and the higher the concentration of these factors. These and other factors may be used as activation indicators of platelets and can be measured in a sample to determine the activation status of platelets in a platelet product from which the sample was taken.

SUMMARY OF THE INVENTION

According to an embodiment of the invention, untested platelets are screened using dynamic light scattering methodologies and segregated into two groups according to the results of the DLS screening: (a) non-activated platelets, and (b) activated platelets. The non-activated platelets are identified as such and designated for transfusion to cancer patients. The activated platelets are identified as such and designated to other, non-cancer patients such as surgical and trauma patients.

According to a further embodiment, aliquots of platelets obtained from a platelet transfusion product are analyzed for activation indicators that are associated with activated platelets, including microparticles, and the concentration of the microparticles is determined. If the level of activation indicators is greater than a predetermined threshold, the platelet product from which the aliquots were obtained is characterized as being activated and transfusion of the platelets is restricted to prevent transfusion to cancer patients, while allowing transfusion into bleeding patients. If the level of microparticles is equal to or less than a predetermined threshold, the platelet product corresponding to the tested aliquot is characterized as being non-activated and transfusion of the platelet product to cancer patients (and other patients) is allowed.

BRIEF DESCRIPTION OF THE DRAWINGS

Further features and advantages of the present invention will become apparent from the following detailed description, taken in combination with the appended drawing, in which:

FIGS. 2 through 7 are graphs generated from data and results from two separate studies to test the effectiveness of the protocols according to the present invention. More specifically.

DETAILED DESCRIPTION OF EMBODIMENTS

Various embodiments and aspects of the present invention will now be described. The term "microparticles" as used herein is understood to mean particles within bodily fluids (such as blood), which have a hydrodynamic radius of less than about 1 micron, and may in one possible embodiment have a hydrodynamic radius of between approximately 20 and 1000 nm, and more preferably in another embodiment may have a hydrodynamic radius of between about 50 nm and 499 nm. The term microparticles as used herein is also intended to include so-called "nano-particles". Microparticles are much smaller than the larger platelets in a platelet rich plasma blood sample for example. This may be seen in exemplary differential interference contrast (DIC) microscopy images of platelet rich plasma samples taken from a cardiovascular disease patient, showing the presence of microparticles in the fluid along with the bigger platelets.

Microparticles indicate platelet activation. As described in detail in, for instance, U.S. Pat. Nos. 8,323,922 and 8,834,129 ("Dynamic Light Scattering for in vitro Testing of Bodily Fluids"), the entire disclosures of which are incorporated herein by this reference and which are licensed by the assignee of the present application, dynamic light scattering methodologies are useful to detect microparticles as an indicator of platelet activation status. Accordingly, the present invention utilizes dynamic light scattering methodologies as described in the referenced patents to screen platelet products for the activation indicators as a measure of activation status, and based on those results make decisions on transfusion of the screened platelet products to patients. According to the invention, activated platelets are not transfused to thrombocytopenic patients but may be transfused to bleeding patients such as surgery and trauma patients where such activated platelets may be more efficacious. On the other hand, dynamic light scattering analysis to identify platelet products characterized as having non-activated platelets allows those platelets to be transfused to thrombocytopenic patients and especially to hematology-oncology patients according to the present invention.

Recently, TGFβ from activated platelets was shown to interfere with the natural recognition of cancer cells by T-cells so that the cancer can evade the immune response and progress. This observation may explain why some people get cancer and some don't and why stress factors play an important role because they likely activate platelets. This also suggests that new blood cancer treatments which are modified T-cells such as CAR T-cells and which are very expensive treatments—known to be over $350,000 per dose—could be inactivated by platelet transfusions that contain activated platelets. However, whether the transfused platelets include activated platelets is not currently part of the calculus or even considered.

Microparticle screening of platelet transfusions could allow for only non-activated platelets to be used for blood cancer patients but one could also screen for any of the other factors which are termed activation indicators because they are regulated by platelet activation. In fact, to oncologists it might make more sense to test for TGFβ if this is the most important immune-reactive agent even if the test itself is more complicated—currently an ELISA, or any of the other inflammatory markers. Since serotonin (5-hydroxytryptamine) is stored in platelets together with TGFβ it could also be implicated.

Essentially, current cancer treatments are mostly immunomodulatory and because platelets are also immune cells (not appreciated by blood bankers and oncologists but well established in the literature in other fields) platelet activation can interfere with the actual treatment and not be supportive at all.

Practical Solutions

To reduce the complexity and risk associated with activated platelet transfusions the present invention comprises methodologies to transfuse thrombocytopenic patients like hematology-oncology patients with exclusively non-activated platelets. The most practical way of achieving this is through routine screening of platelet units in the hospital blood bank and selective allocation of platelets, with non-activated platelets being exclusively transfused to thrombocytopenic patients such as patients having a hematologic malignancy.

Previous studies have shown an inverse correlation between microparticle content and platelet count increments after transfusion. Additionally, proof of concept studies of platelet samples analyzed with DLS using ThromboLUX instruments showed reductions in platelet usage per patient of 12-17%. It is therefore believed that by minimizing hematology-oncology patients' exposure to activated platelets, the chance that these patients develop non-immune refractoriness is greatly reduced, and therefore patients require fewer transfusions on average.

Two separate studies were conducted to test the effectiveness of screening platelets to selectively allocate platelets for transfusion according to the invention. The first study was at a pediatric hospital and the second was at an adult hospital. Both studies are described below.

Pediatric Hospital Study

As part of routine practice in a blood bank, the activation status of platelet transfusions was analyzed with a commercially available instrument sold under the name ThromboLUX, manufactured by the applicant and assignee for the present application. These instruments analyze platelet samples using dynamic light scattering (herein, "DLS") methodologies and instruments as described in U.S. Pat. Nos. 7,341,873 and 8,877,458; the entire disclosures of which are incorporated herein by this reference and each of which is licensed by the assignee of the present application. DLS was used to determine the activation status of platelet transfusions to minimize hematology-oncology patients' exposure to activated platelets. The hospital maintained all its pre-existing platelet transfusion policies and clinicians were blinded to the study.

The ThromboLUX utilizes DLS to determine the platelet activation status of a platelet concentrate. The instrument determines platelet activation status by measuring the microparticle content in a representative 100 μL sample taken from a platelet bag using sterile techniques. Platelets stored in 100% plasma are characterized as non-activated if their microparticle content is 15% or lower, while platelets with microparticle content greater than 15% are characterized as activated platelets. A threshold value of 15% may be used as an indicator of activated platelets; if the Microparticle content of a DLS-tested aliquot is less than or equal to the threshold value the corresponding platelet product from which the tested aliquot was obtained will be characterized as non-activated. It will be appreciated that the threshold value may be variable based on the situation and the intended transfusion patient's particular condition. For example, the threshold value may be at least 10% in some circumstances.

The study was designed to assess if platelet activation status-based inventory management would result in a reduction in platelet utilization. Two metrics for platelet utilization were assessed: Proportion of Complex Cases (patients who received >10 transfusion in a 30-day period), and Mean Transfusions per Patient (TPP).

The Intent to Treat analysis found a statistically significant reduction in Complex Cases of 55% (1-sided p-value=0.035) as well as a nearly statistically significant reduction of 32% in mean TPP (1-sided p-value=0.059).

A significant number of hematology-oncology patients received activated platelets due to inventory limitations and ABO matching policy, however, the site always selected the least activated platelets in inventory if non-activated platelets that met their policy criteria were not available. To accommodate this limitation a Per Protocol analysis was also conducted.

The Per Protocol analysis found a statistically significant reduction in Complex Cases of 74% (1-sided p-value=0.001) and a statistically significant reduction in mean TPP of 44% (1-sided p-value=0.01).

This study confirmed previous findings that minimizing the transfusion of activated platelets to hematology-oncology patients results in reduced platelet utilization by preventing the development of Complex Cases that require massive transfusion support.

An evaluation was conducted at a large pediatric hospital to determine if allocating inventory based on platelet activation status, as determined by DLS analysis with the ThromboLUX instrument, would result in lower platelet transfusion requirements for hematology-oncology patients.

The study was conducted with hematology-oncology patients as the target patient population. The study used a quasi-experimental time-series design comparing a control period as the Baseline to a DLS analysis implementation period as the Evaluation. The transfusion data from a prior four-month Baseline period were compared with the four-month Evaluation period for the study.

Over the four-month study period DLS analysis was used as part of routine practice in the blood bank. The blood bank staff tested all platelet units upon receipt from their blood supplier. DLS analysis reported the activation status of a tested platelet unit as activated or non-activated based on the microparticle content. The blood bank staff kept a dual inventory and planned to allocate non-activated platelets to hematology-oncology patients requiring prophylactic transfusions and activated platelets to actively bleeding surgical and trauma patients.

Figure 1:
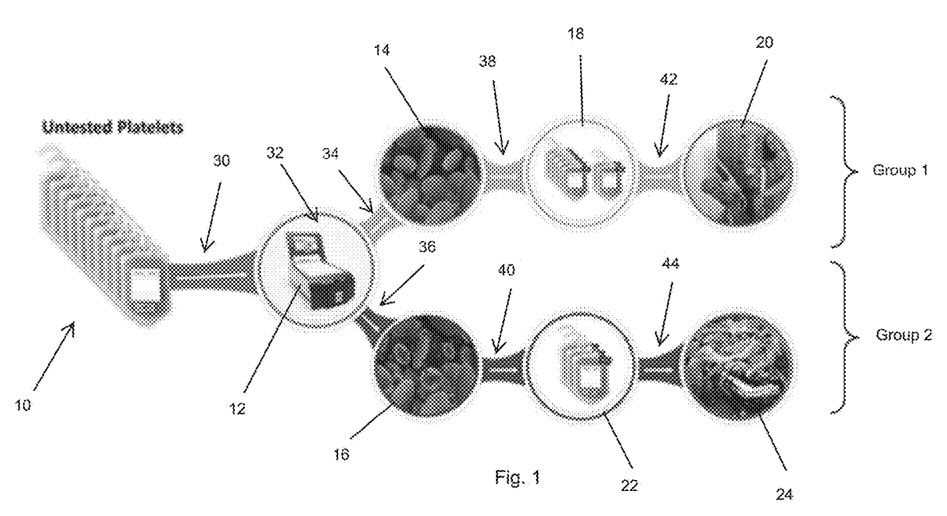
FIG. 1 is a schematic illustration of a platelet activation status-based inventory management and platelet allocation plan according to the present invention.

The allocation plan is illustrated in FIG. 1. Specifically, as shown in FIG. 1 untested platelets 10 are screened using dynamic light scattering methodologies (as detailed herein using the ThromboLUX instrument 12) and segregated into two groups according to the results of the DLS screening: (a) Group 1 representing non-activated platelets 14, and (b) and Group 2 representing activated platelets 16. The non-activated platelets 14 are identified as such, for instance by appropriate tagging 18 and designated for transfusion to a first category of patients, thrombocytopenic patients 20. The activated platelets 16 are identified as such with tagging 22 and designated to a second category of patients, non-cancer patients, such as surgical and trauma patients 24. The Group 1 category of platelet products corresponding to the tested sample are preferably transfused to patients in the first category, but may also be transfused to patients in the second category. On the other hand, the Group 2 category of platelet products that correspond to the tested sample may be transfused only to patients in the second category. The DLS analysis screens for at least one sample characteristic or activation indicator that is indicative of platelet activation. More preferably, microparticles are used as the referenced activation indicator or sample characteristic.

The allocation plan outlined in FIG. 1 thus contemplates the following procedure:
 a. obtaining a sample aliquot from a platelet product (such as a unit of platelets); step 30;
 b. analyzing the sample using DLS for at least one sample characteristic to determine the activation status of the platelets; step 32;
 c. if the analysis indicates that less than or equal to a predetermined threshold of platelets are activated, segregating the platelet product that corresponds to the analyzed sample to a first group of platelet products; step 34;
 d. if the analysis indicates that more than the predetermined threshold of platelets are activated, segregating the platelet product that corresponds to the analyzed sample into a second group of platelet products; step 36;
 e. tagging the platelet product in the first group as being transfusable to a first patient group; step 38;
 f. tagging the platelet product in the second group as being transfusable to a second patient group; step 40;
 g. transfusing the tagged platelet products to patients in designated groups; steps 42 representing patients in the first patient group, and step 44 representing patients in the second patient group.

The hospital maintained all its pre-existing platelet transfusion policies including transfusion trigger, ABO-matching policy, and donor exposure minimization practices. When it was not possible to allocate a non-activated platelet unit to a hematology-oncology patient due to inventory limitations or transfusion policy, the platelet unit with the lowest microparticle content (least activated) was allocated instead.

The primary outcome metric for the evaluation was a reduction in the proportion of Complex Cases. Complex Cases were defined as hematology-oncology patients who received 10 or more platelet transfusions within any 30-day window during the evaluation.

The secondary outcome was a reduction in average Transfusions Per Patient (TPP).

The statistical analysis for this study was conducted by a third-party biostatistician group. The statistical methods described are summarized below.

The Baseline period included all hematology-oncology patients who received a platelet transfusion at any location within the pediatric hospital during a four month period. Similarly, the Evaluation period included all hematology-oncology patients who received platelet transfusions at any location within the pediatric hospital during the four month period of the study. A data lock date was established to capture any patient deaths or other events which occurred within a week of the end of the Evaluation period.

The data used for comparison between the Baseline and the Evaluation periods included admission and discharge dates for each patient, the date of each transfusion, death dates for any patient known to have died between the beginning of the Baseline period, and the date of the data lock.

The effect of DLS analysis based inventory management is predicted to minimize the risk of a patient becoming refractory to platelet transfusions by preventing the transfusion of activated platelets to hematology-oncology patients. Thus, patients that may have been exposed to activated platelets prior to the start of the evaluations were excluded from analysis. To avoid biasing the data the following inclusion criteria were applied to both the Baseline and Evaluation periods. The Intent to Treat analysis incorporated all transfusions and all patients that fit within the following criteria.

First available admission date was following the start of the period

If admission dates were not available, patient's first transfusion must have been >7 days after the start of the period Due to inventory constraints and other transfusion considerations it was not possible for the evaluating hospital to transfuse exclusively non-activated platelets to the hematology-oncology patients involved in the evaluation. Due to the risk of data biasing it was not possible to remove all patients who had received activated platelets from the analysis. As a compromise between a strict Per Protocol analysis and the Intent to Treat analysis the following rules were applied:

A protocol non-compliance event was defined as receipt of three consecutive activated transfusions within an admission by a hematology-oncology patient.

Transfusions occurring after a non-compliance event were excluded from the Per Protocol analysis. All transfusions preceding the non-compliance event and the three transfusions of the non-compliance event were included in the Per Protocol analysis The statistical methods were conducted to determine the level of reduction in Complex Cases and TPP, therefore one-sided statistical tests were selected for both outcome metrics.

All statistical analysis was conducted using the open source statistical computing platform R. To model the mean TPP an over dispersed-Poisson model with a period effect was used. This model accounted for the extra-Poisson variability in the data and was fit using a GEE approach (R statistical computing platform v3.5, glm function with family='quasipoisson'). Inference was performed using a one-sided Wald test of the period coefficient. Confidence intervals and p-values were confirmed using a bootstrap and a permutation test, respectively.

Logistic regression was used to compare the proportion of Complex Cases between the two periods. Inference was performed using a one-sided Wald test of the period coefficient.

During the Baseline period 101 hematology-oncology patients were admitted. Of the 101 patients, 14 received over 10 transfusions within a 30-day period resulting in a Complex Case rate of 14% (95% CI: 8%, 22%). A total of 682 platelets were transfused to the 101 patients resulting in a mean TPP of 6.8 (95% CI: 4.9, 9.3).

The Intent to Treat analysis showed that during the Evaluation period 112 patients were admitted. Of the 112 patients, 7 were identified as Complex Cases resulting in a Complex Case rate of 6% (95% CI: 3%, 13%). This represented a 55% reduction in the proportion of Complex Cases compared to the baseline value of 14% (1-sided p-value=0.035).

Collectively the 112 patients received 508 transfusions for a mean TPP of 4.5 (95% CI: 3.1, 6.6). This represented a reduction of 32% from the baseline TPP of 6.8 (1-sided p-value=0.059).

Per Protocol analyses are commonly performed to investigate the effect of non-compliance with the protocol. In this study, 7 patients received 3 or more consecutive activated platelet transfusions. Since the non-compliant transfusions were expected to impact subsequent transfusion outcomes, the transfusions that followed the non-compliance event were removed for the Per Protocol analysis.

The Per Protocol analysis also included 112 patients. Of these 112 patients there were 4 Complex Cases resulting in a Complex Case rate of 4% (95% CI: 2%, 10%). This represents a 74% reduction in the proportion of Complex Cases compared to the baseline value of 14% (1-sided p-value=0.01).

The 112 patients analyzed collectively received 426 transfusions Per Protocol leading to a TPP of 3.8 (95% CI: 2.6, 5.6). This represented a reduction of 44% from the baseline TPP of 6.8 (1-sided p-value=0.01).

Figure 2:
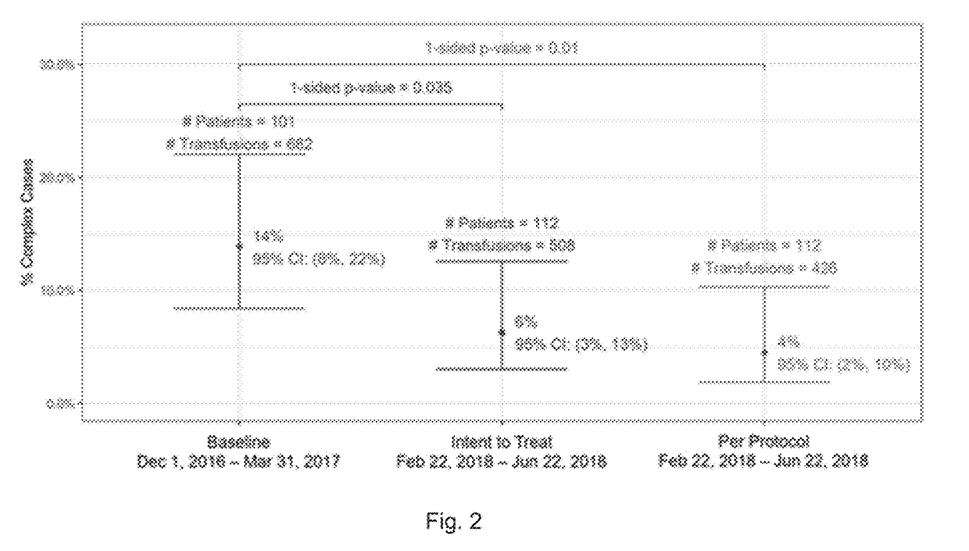
FIG. 2 is a graphic representation of the proportion of complex cases by analysis population for a study at a pediatric hospital using protocols according to the present invention.
Figure 3:
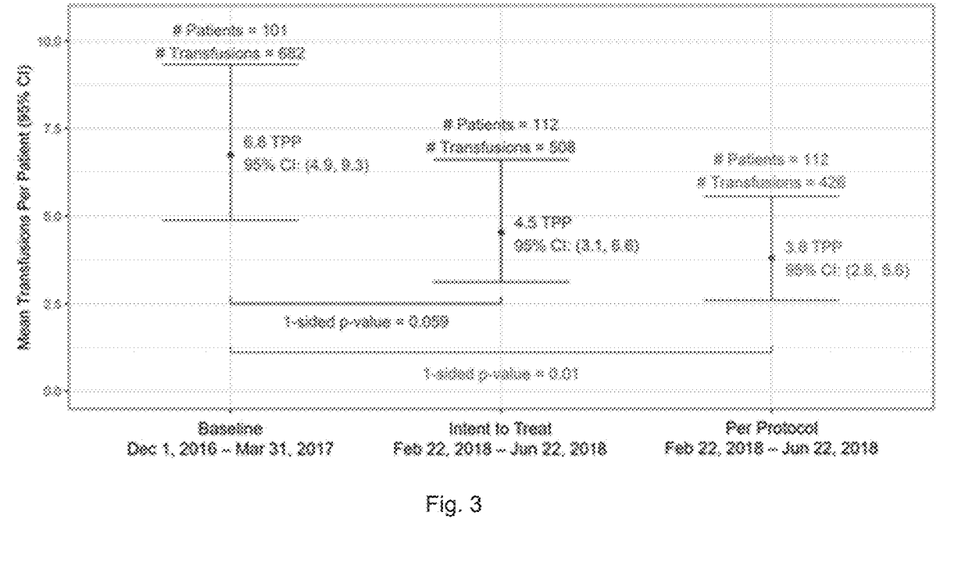
FIG. 3 is a graphic representation of the mean transfusions per patient by analysis population for the study referenced in FIG. 2, using protocols according to the present invention.

Table 1 provides a summary of the distribution of patients and transfusions by analysis population. Table 2 provides a summary of the two analysis populations compared to the Baseline. The reduction in the proportion of Complex Cases and reduction in TPP for the two analysis populations are presented in FIGS. 2 and 3, respectively.

TABLE 1

Number of Patients, Number of Transfusions and Number of Complex Cases by Analysis Population

|  | Baseline | Intent to Treat | Per Protocol |
|---|---|---|---|
| Patients | 101 | 112 | 112 |
| Transfusions | 682 | 508 | 426 |
| Complex Cases | 14 | 7 | 4 |

TABLE 2

Summary of Outcome Metrics by Analysis Population

| | Intent to Treat | | Per Protocol | |
|---|---|---|---|---|
| | Complex Case % (95% CI) | Mean TPP (95% CI) | Complex Case % (95% CI) | Mean TPP (95% CI) |
| Baseline | 14% (8%, 22%) | 6.8 (4.9, 9.3) | 14% (8%, 22%) | 6.8 (4.9, 9.3) |
| Evaluation | 6% (3%, 13%) | 4.5 (3.1, 6.6) | 4% (2%, 10%) | 3.8 (2.6, 5.6) |
| % Reduction | 55% | 32% | 71% | 44% |
| 1-sided p-value | 0.059 | 0.035 | 0.01 | 0.01 |

This evaluation confirms previous findings that allocating inventory based on platelet activation status, as determined by DLS analysis with the ThromboLUX instrument, results in lower average transfusion per patient requirements. Furthermore, this evaluation collected patient-linked data and allowed confirmation of the hypothesis that the reduction in TPP is primarily due to a reduction in Complex Cases.

The Intent to Treat analysis reached statistical significance for the reduction in complex cases and was very near to statistical significance for a reduction in mean TPP. This implies that despite transfusions of activated platelets to quite a few patients there is an overall benefit of minimizing the transfusion of activated platelets to hematology-oncology patients. The Per Protocol analysis showed statistically significant reductions in both the proportion of Complex Cases and the mean TPP.

The increased difference from Baseline and greater statistical confidence found in the Per Protocol analysis shows that the expected improvement in transfusion results would likely increase if the hospital were able to follow the platelet allocation protocol more strictly and prevent transfusions of activated platelets to hematology-oncology patients.

The reduction of platelet transfusions and reduction in the number of Complex Cases treated according to the invention described herein will positively impact the cost to treat hematology-oncology patients. Understanding the complete cost to transfuse a patient is a complex topic which varies greatly between institutions. The cost per transfusion at the study site was estimated at $912.

By reducing the TPP by 32% the hospital saved 258 platelet transfusions during the 4-month evaluation. If they had been able to adhere more closely to the protocol the Per Protocol analysis projects a 44% reduction and the hospital would have saved 336 platelets during the 4-month evaluation. This leads to expected savings of $705,888 via the Intent to Treat analysis or $919,296 via the Per Protocol analysis.

An alternative way to assess the economic impact is to base the savings on the reduction of Complex Case patients, as this is the primary impact of DLS analysis. A transfusion frequency of more than 10 transfusions within a 30-day period strongly suggests platelet refractoriness. With this assumption, the cost savings can be estimated based on the difference in cost to treat refractory and non-refractory patients. The cost difference between these two patient categories found in prior studies, adjusted for inflation is $96,791. By reducing the rate of Complex Cases by 55%, the evaluating hospital saved $871,119 during the evaluation and could potentially save $2,613,357 annually. Had the hospital followed the protocol more strictly, they could have potentially reduced the rate of Complex Cases by 71%, resulting in savings of $1,064,701, and a potential annual savings of $3,194,103.

Regardless of how the estimate of savings is conducted, the savings from sizably reducing complex platelet transfusion patients and thus reducing platelet transfusion is significant especially in times of shrinking budgets for transfusion services across the country.

Adult Academic Hospital Study

The second study, which as noted above was conducted in an adult academic hospital is summarized below and the results from the second study are consistent with the first study discussed above. The basic parameters for the second study were the same as the parameters for the first study, with DLS analysis with the ThromboLUX instrument providing the analytical basis for evaluating the activation status of transfused platelets.

In the second study, two important clinical outcomes, average count increments and average time to next transfusion, were investigated for before ("Prior to Activated Transfusion") and after ("Post Activated Transfusion") hematology-oncology patients received activated platelets, a non-compliance with the study protocol.

Following an activated platelet transfusion, the average count increment was 22% lower, 17.95 for the Post Activated Transfusion group (95% confidence: 14.20, 21.71) compared to 22.88 for the Prior to Activated Transfusion group (95% confidence: 18.4, 27.3) (1-sided Wald p-value=0.002).

In addition, the transfusion interval decreased by 1.38 days or 32% after patients received an activated platelet transfusion. The average time to next transfusion was 2.58 days for the Post Activated Transfusion group (95% confidence: 1.91, 3.49) compared to 3.96 days for the Prior to Activated Transfusion group (95% confidence: 2.98, 5.27) (1-sided Wald p-value=0.002).

The study also showed reductions in Complex Cases and average Transfusions Per Patient and suggested that these reductions might be improved with better protocol compliance.

As noted, the second study was conducted at an academic hospital with hematology-oncology patients as the target patient population. The study used a quasi-experimental time-series design comparing a control period as the Baseline to a ThromboLUX implementation period as the Evaluation. The transfusion data from the 88-day Baseline period were compared with an 88-day Evaluation period.

Over the 88-day Evaluation period DLS analysis was used as part of routine practice in the blood bank. The blood bank staff tested all platelet units upon receipt from their blood supplier. The DLS analysis reported the activation status of a tested platelet unit as activated or non-activated, based on the microparticle content. The blood bank staff kept a dual inventory and planned to allocate non-activated platelets to hematology-oncology patients requiring prophylactic transfusions, and activated platelets to actively bleeding surgical and trauma patients. The allocation plan is the same as the allocation plan utilized in the first study and is illustrated in FIG. 1.

As with the first study, the hospital maintained all its pre-existing platelet transfusion policies including transfusion trigger, ABO-matching policy, and HLA-matching policy. When it was not possible to allocate a non-activated platelet unit to a hematology-oncology patient due to inventory limitations, or transfusion policy, an activated platelet unit was allocated.

The sporadic occurrence of hematology-oncology patients receiving activated platelets allowed for analysis of the effects of an activated platelet transfusion on the count increments and transfusion intervals to transfusions that followed (regardless of the activation status of the following platelet transfusions).

The primary clinical outcome metric for the evaluation was the difference in average count increment (CI) obtained with non-activated transfusions prior to any activated transfusions compared to the average CI subsequent to an activated platelet transfusion (including the outcome of the activated transfusion).

The secondary clinical outcome metric was the difference in average time to next transfusion between transfusions prior to an activated transfusion and the transfusions following an activated transfusion.

There were two platelet utilization outcome metrics assessed. The first looked at a reduction in the proportion of Complex Cases. The medical staff at the evaluation site defined Complex Cases as any hematology-oncology patient who received 5 or more platelet transfusions within any 30-day window during the evaluation. The second platelet utilization outcome was a reduction in average Transfusions Per Patient (TPP).

The statistical analysis for this study was conducted by a third-party biostatistician group, and the statistical methods are summarized below.

The Baseline period included all hematology-oncology patients who received a platelet transfusion at any location within the hospital during the 88 day period. Similarly, the Evaluation period included all hematology-oncology patients who received platelet transfusions at any location within the hospital during the 88 days of the study.

The data used for comparison between the Baseline and the Evaluation periods included admission and discharge dates for each patient, the date of each transfusion, platelet counts before and after transfusion, and death dates for any patient known to have died between the beginning of the Baseline period, and the date of the data lock. The data collection was conducted with Institutional Research Ethics Board approval.

The benefit of DLS screening of platelet activation status is to reduce the risk of future failed transfusions and the development of non-immune refractoriness. To enable an unbiased estimate of this benefit, only subjects admitted after the start of the DLS analysis Evaluation period, and who had not received outpatient transfusions within 21 days of the start of the period were enrolled in the study. The 21-day interval was selected following a sensitivity analysis using a 95% confidence interval on the maximum length of time between outpatient transfusions. These patients were called de novo patients. Thus, the criteria for inclusion in analysis can be summarized as:

First available admission date is following the start of the period

Patient did not receive transfusions as an outpatient within 21 days of the start of the period The "Prior to Activated Transfusion" analysis group was comprised of all transfusions given to de novo patients during the Evaluation before the patient received their first activated transfusion. Non-activated transfusions to patients who never received an activated transfusion were also included in this group.

The "Post Activated Transfusion" analysis group was comprised of the first activated transfusion received by a de novo patient during the Evaluation, and all subsequent transfusions received by that patient.

The Intent to Treat population included all de novo patients in the Baseline and Evaluation period regardless of the activation status of the platelets they received.

Per Protocol analyses are commonly performed to investigate the effect of non-compliance with the protocol. Strict Per Protocol analysis would involve the exclusion of all patients that received an activated transfusion. Since the allocation of activated platelets was random, it is more likely that a patient with a condition requiring more transfusions would receive an activated transfusion than a patient with a condition requiring fewer transfusions. Thus, a strict Per Protocol analysis could bias the data. To better assess the impact of non-compliant transfusions (activated transfusions to evaluation patients) five compliance populations were defined.

The definitions of the five compliance populations in order of increasing strictness were: first transfusion, first three transfusions, first five transfusions, first ten transfusions and all transfusions received by a patient were non-activated. The last group only includes patients who exclusively received non-activated transfusions (Per Protocol).

The statistical methods were conducted to assess superiority of the intervention; thus one-sided statistical tests were selected for all outcome metrics. All statistical analysis was conducted using the open source statistical computing platform R.

To model count increments: a linear mixed effects model was fit with count increment as the outcome, where an indicator for whether the transfusion was activated or followed the first activated transfusion was a fixed effect, and patient ID was a random effect.

To model the time between transfusions, the following was used: a mixed effects Poisson model with an intercept term, an indicator for whether the transfusion was after the first activated transfusion, a random effect for patient, and an offset term with the log number of days between transfusions.

Logistic regression was used to compare the proportion of Complex Cases between the two periods. Inference was performed using a one-sided Wald test of the period coefficient.

To model the mean TPP an over dispersed-Poisson model with a period effect was used. This model accounted for the extra-Poisson variability in the data and was fit using a GEE approach (R statistical computing platform v3.5, glm function with family='quasipoisson'). Inference was performed using a one-sided Wald test of the period coefficient.

Table 3 provides a summary of the distribution of patients and transfusions for the two analysis groups for clinical outcome.

|  | Prior to Activated Transfusion | Post Activated Transfusion |
| --- | --- | --- |
| Patients | 103 | 37 |
| Transfusions | 304 | 205 |

The average count increment in the Prior to Activated Transfusion group was 22.88 (95% confidence: 18.4, 27.3). The average count increment in the Post Activated Transfusion group was 17.95 (95% confidence: 14.20, 21.71). The difference in average count increment was 4.93 for a count increment reduction of 22% in the Post Activated Transfusion group. This difference was statistically significant at the 0.05 level (1-sided Wald p-value=0.002).

Figure 4:
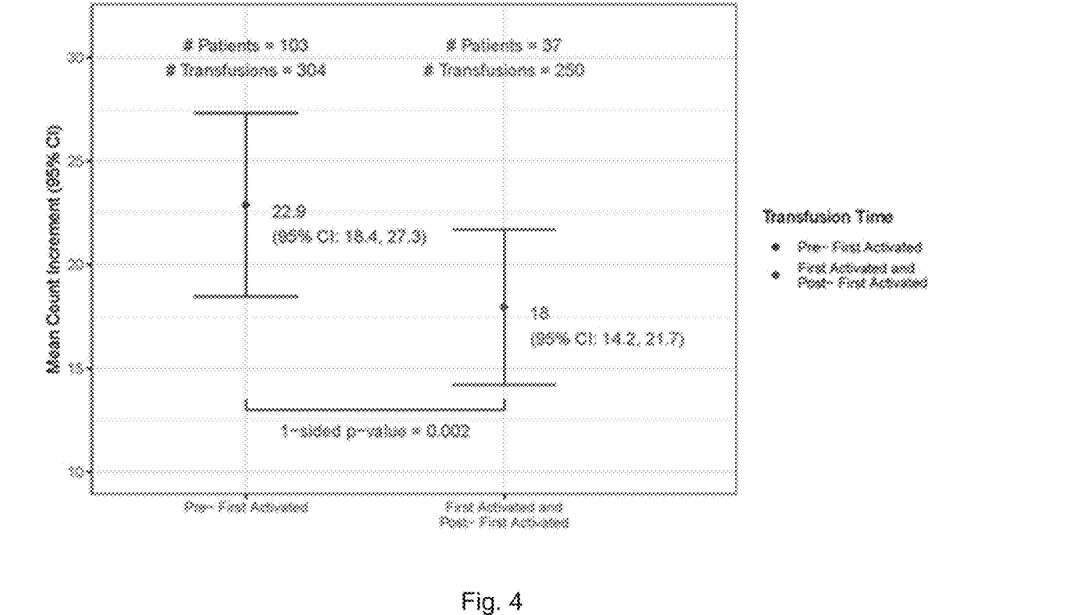
FIG. 4 is a graphic representation of mean count increments by patient from a study at an adult academic hospital using protocols according to the present invention.

Table 4 provides a summary of the count increment and time to next transfusion for the two analysis populations along with the reduction found in the Prior to Activated Transfusion group. FIG. 4 illustrates the distribution of average count increments by patient in the two analysis populations.

|  | Prior to Activated Transfusion | Post Activated Transfusion | % Difference | p-value |
| --- | --- | --- | --- | --- |
| Average count increment | 22.88 (18.4, 27.3) | 17.95 (14.20, 21.17) | 22% | 0.002 |

The average time to next transfusion in the Prior to Activated Transfusion group was 3.96 days (95% confidence: 2.98, 5.27). The average time to next transfusion in the Post Activated Transfusion group was 2.58 days (95% confidence: 1.91, 3.49). The difference in average time to next transfusion was 1.38 days for a reduction of 32% in the Post Activated Transfusion group. This difference was statistically significant at the 0.01 level (1-sided Wald p-value=0.002).

TABLE 5

Average time to next transfusion by analysis

|  | Prior to Activated Transfusion | Post Activated Transfusion | % Difference | p-value |
|---|---|---|---|---|
| Time to next transfusion | 3.96 (2.98, 5.27) | 2.58 (1.91, 3.49) | 35% | 0.002 |

During the Baseline period 112 de novo hematology-oncology patients were admitted. Of the 112 patients, 31 received over 5 transfusions within a 30-day period resulting in a Complex Case rate of 27.7% (95% confidence: 20.2%, 36.7%). A total of 592 platelets were transfused to the 112 patients resulting in a mean TPP of 5.29 (95% confidence: 4.20, 6.66).

Table 6 provides a summary of the distribution of patients and transfusions by analysis population.

TABLE 6

Number of Patients, Number of Transfusions and Number of Complex Cases by Analysis Population

|  | Baseline | Intent to Treat | Per Protocol (All Compliant) |
|---|---|---|---|
| Patients | 112 | 116 | 79 |
| Transfusions | 592 | 554 | 220 |
| Complex Cases | 31 | 26 | 7 |

The Intent to Treat analysis showed that 116 de novo patients were admitted during the Evaluation period. Of the 116 patients, 26 were identified as Complex Cases (>5 transfusions in 30 days) resulting in a Complex Case rate of 22.4% (95% confidence: 15.7%, 30.9%). This represented a 19% reduction in the proportion of Complex Cases compared to the Baseline value of 27.7 (1-sided p-value=0.18).

There were 79 de novo patients compliant for all their transfusions during the Evaluation period. Of the 79 patients, 7 were identified as Complex Cases (>5 transfusions in 30 days) resulting in a Complex Case rate of 8.9% (95% confidence: 4.3%, 17.4%). This represented a 68% reduction in the proportion of Complex Cases compared to the Baseline value of 27.7 (1-sided p-value=0.001).

Figure 6:
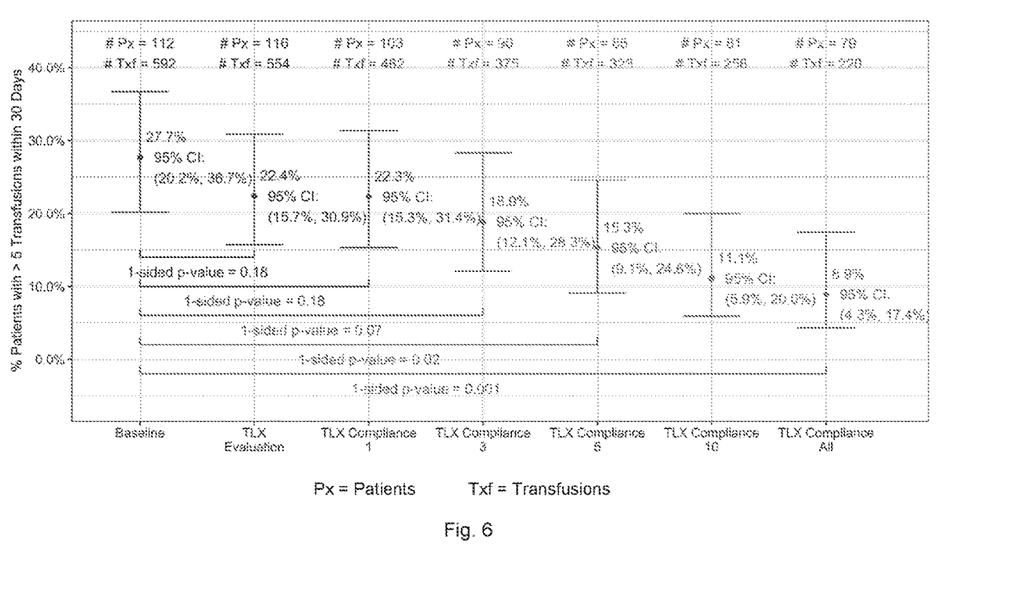
FIG. 6 is a graphic representation of proportion of complex cases in all compliance analysis populations for the study referenced in FIG. 4, using protocols according to the present invention.

Table 7 provides a summary of the proportion of complex cases in the Intent to Treat and Per Protocol analysis populations compared to the Baseline. FIG. 6 shows the proportion of complex cases in all compliance analysis populations.

TABLE 7

Summary of Complex Case by Analysis Population

|  | Intent to Treat | Per Protocol |
|---|---|---|
| Baseline Complex Cases | 27.7% (20.2%, 36.7%) | |
| Evaluation Complex Cases | 22.4% (15.7%, 30.9%) | 8.9% (4.3%, 17.4%) |
| % Reduction | 19% | 68% |
| 1-sided p-value | 0.18 | 0.001 |

The 116 de novo patients collectively received 554 transfusions for a mean TPP of 4.78 (95% confidence: 3.76, 6.06). This represented a reduction of 9.6% from the Baseline TPP of 5.29 (1-sided p-value=0.27).

The 79 fully compliant patients collectively received 220 transfusions for a mean TPP of 2.78 (95% confidence: 1.99, 3.89). This represented a reduction of 47% from the Baseline TPP of 5.29 (1-sided p-value <0.001).

Figure 7:
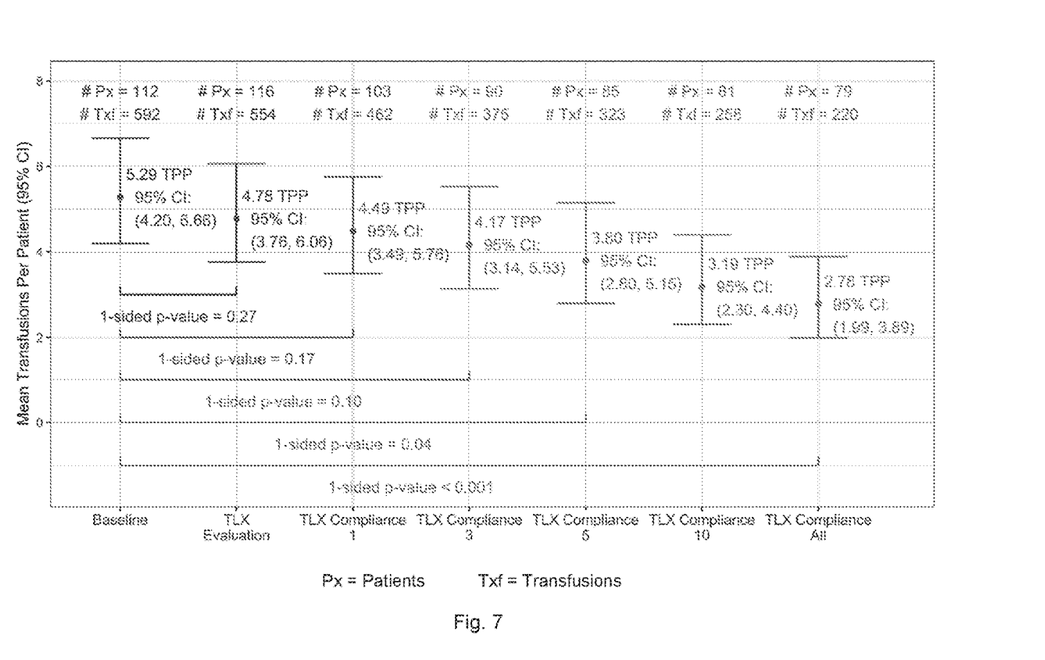
FIG. 7 is a graphic representation of mean transfusions per patient for all compliance analysis populations for the study referenced in FIG. 4, using protocols according to the present invention.

Table 8 provides a summary of the mean transfusions per patient in the Intent to Treat and Per Protocol analysis populations compared to the Baseline. FIG. 7 shows the mean transfusions per patient for all compliance analysis populations.

TABLE 8

Summary of Mean TPP by Analysis Population

|  | Intent to Treat | Per Protocol |
|---|---|---|
| Baseline TPP | 5.29 (4.20, 6.66) | |
| Evaluation TPP | 4.78 (3.1, 6.6) | 2.78 (1.99, 3.89) |
| % Reduction | 9.6% | 47% |
| 1-sided p-value | 0.27 | <0.001 |

This evaluation of DLS analysis of platelet activation status using the ThromboLUX instrument investigated the direct impact of activated platelets on the commonly used clinical outcomes of count increment and time to next transfusion. This confirms previous findings that platelet activation status has an impact on count increment. The results show the negative effects on a patient when receiving even just one activated transfusion during their course of treatment.

The findings of this study related to platelet utilization showed reductions in Complex Cases and mean transfusions per patient. These results were not statistically significant for the Intent to Treat analysis, but the Per Protocol analysis suggested that better protocol compliance would likely show these results to be statistically significant. However, the exact reduction in these values cannot be determined due to the previously discussed selection bias in the Per Protocol analysis group.

The $1^{st}$ transfusion compliance group analysis showed that 103 de novo patients were admitted with their first transfusion being non-activated. Of the 103 patients, 23 were identified as Complex Cases (>5 transfusions in 30 days) resulting in a Complex Case rate of 22.3% (95% confidence: 15.3%, 31.4%). This represented a 19% reduction in the proportion of Complex Cases compared to the baseline value of 27.7 (1-sided p-value=0.18).

Collectively the 103 first transfusion compliant patients received 462 transfusions for a mean TPP of 4.49 (95% confidence: 3.49, 5.76). This represented a reduction of 15% from the baseline TPP of 5.29 (1-sided p-value=0.17).

There were 90 de novo patients compliant for all their first three transfusions. Of the 90 patients, 17 were identified as Complex Cases (>5 transfusions in 30 days) resulting in a Complex Case rate of 18.9% (95% confidence: 12.1%, 28.3%). This represented a 32% reduction in the proportion of Complex Cases compared to the baseline value of 27.7 (1-sided p-value=0.07).

Collectively the 90 first three transfusion compliant patients received 375 transfusions for a mean TPP of 4.17 (95% confidence: 3.14, 5.53). This represented a reduction of 21% from the baseline TPP of 5.29 (1-sided p-value=0.10).

There were 85 de novo patients compliant for all their first five transfusions. Of the 85 patients, 13 were identified as Complex Cases (>5 transfusions in 30 days) resulting in a Complex Case rate of 15.3% (95% confidence: 9.1%, 24.6%). This represented a 45% reduction in the proportion of Complex Cases compared to the baseline value of 27.7 (1-sided p-value=0.02).

Collectively the 85 first five transfusion compliant patients received 323 transfusions for a mean TPP of 3.80 (95% confidence: 2.80, 5.15). This represented a reduction of 28% from the baseline TPP of 5.29 (1-sided p-value=0.04).

There were 81 de novo patients compliant for all their first ten transfusions. Of the 81 patients, 9 were identified as Complex Cases (>5 transfusions in 30 days) resulting in a Complex Case rate of 11.1% (95% confidence: 5.9%, 20.0%). This represented a 60% reduction in the proportion of Complex Cases compared to the baseline value of 27.7 (1-sided p-value <0.01).

Collectively the 81 first ten transfusion compliant patients received 258 transfusions for a mean TPP of 3.19 (95% confidence: 2.30, 4.40). This represented a reduction of 40% from the baseline TPP of 5.29 (1-sided p-value <0.01).

Figure 5:
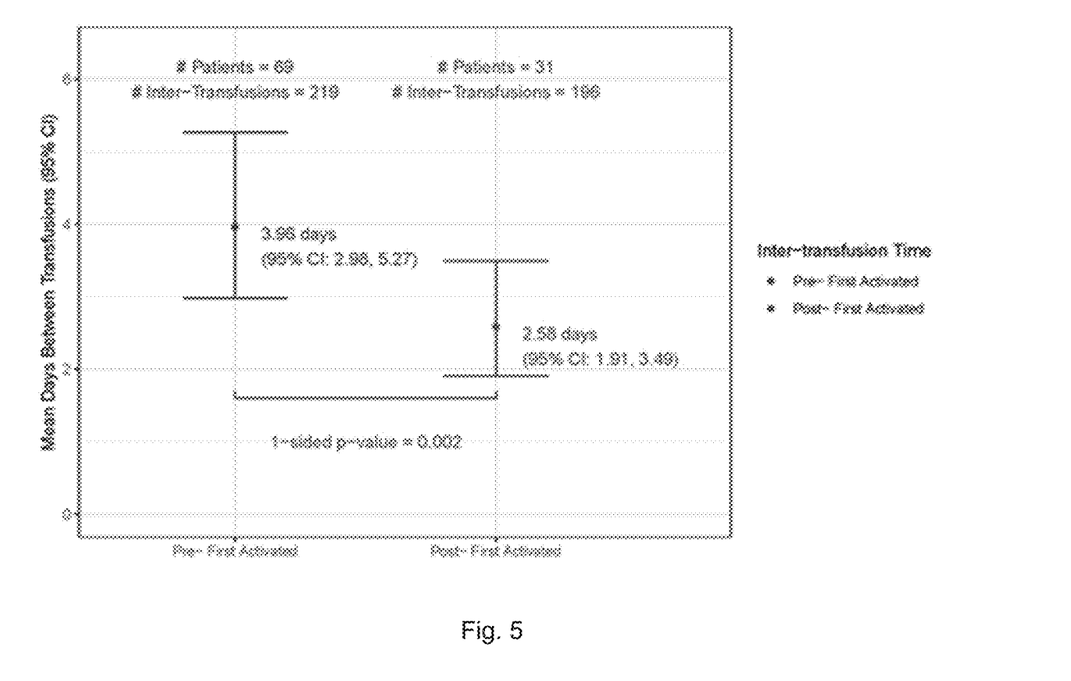
FIG. 5 is a graphic representation of time to next transfusion in days by analysis population for the study referenced in FIG. 4, using protocols according to the present invention.

Screening platelets using DLS methodologies and instruments to identify activated and non-activated platelets according to Microparticle content, then segregating the platelets according to their activation status and transfusing only non-activated platelets into hematology-oncology patients has an effect on clinical outcomes. With reference now to FIG. 5, There was a statistically significant decrease in the time between transfusions received pre first activated transfusion and post-first activated transfusion. The mean time between transfusions was 3.96 days (95% CI: 2.98, 5.27) prior to the first activated transfusion, and 2.58 days (95% CI: 1.91, 3.49) after the first activated transfusion (1-sided Wald p-value=0.002). And there was a statistically significant decrease, at the 0.05 one-sided level, in count increment in the after or including the first activated transfusion compared to before (FIG. 4). The mean count increment prior to activated transfusions was 22.9 (95% CI: 18.4, 27.3), while the mean count increments including and after the first activated transfusion was 18 (95% CI: 14.2, 21.7, 1-sided p-value=0.002).

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

The invention claimed is:

1. A method of assessing platelets prior to transfusion of the platelet product, comprising the steps of:
   a. using a dynamic light scattering (DLS) instrument, analyzing an aliquot of platelets for at least one sample characteristic that correlates to platelet activation to measure the at least one sample characteristic in the aliquot, wherein the at least one sample characteristic comprises the concentration of microparticles in the aliquot;
   b. comparing the measurement of the at least one sample characteristic to a predetermined threshold value;
   c. if the comparison in step b. indicates that the measurement of the at least one sample characteristic is equal to or less than the predetermined threshold, segregating the corresponding platelet product into a first category;
   d. if the comparison in step b. indicates that the measurement of the at least one sample characteristic is more than the predetermined threshold, segregating the corresponding platelet product into a second category;
   e. allocating the platelet product in the first category for transfusion to a first patient group;
   f. allocating the platelet product in the second category for transfusion to a second patient group.

2. The method according to claim 1 in which the first patient group consists of patients with thrombocytopenia and a need to increase their platelet count.

3. The method according to claim 2 in which the patients are cancer patients.

4. The method according to claim 3 in which the cancer patients have a hematologic malignancy.

5. The method according to claim 1 in which the second patient group consists of actively bleeding patients.

6. The method according to claim 5 including restricting the platelet product in the second category to transfusion only to the second patient group.

7. The method according to claim 2 including transfusing the platelet product in the first category to patients in the first group or the second group.

8. The method according to claim 1 in which the hydrodynamic radius of the microparticles in the aliquot is less than 1 micron.

9. The method according to claim 8 in which the concentration of microparticles in the aliquot correlates to the level of activated platelets in the aliquot.

10. The method according to claim 8 in which the predetermined threshold is characterized as the microparticle content in the aliquot being at least 10%.

11. A method of assessing platelets prior to transfusion of the platelets, comprising the steps of:
    a. obtaining a sample from a platelet product in a transfusion inventory and testing the sample using dynamic light scattering to determine the measurement of one or more activation indicators that correlate with platelet activation, and wherein the one or more activation indicators comprise microparticles;
    b. if the measurement of the one or more activation indicators is below a threshold value, segregating the platelet product from which the sample was obtained into a first transfusion group and allocating transfusion of platelets in the first transfusion group to thrombocytopenic patients
    c. if the measurement of the one or more activation indicators is above a threshold value, segregating the platelet product from which the sample was obtained into a second transfusion group and preventing transfusion of platelets in the second transfusion group to thrombocytopenic patients.

12. The method according to claim 11 wherein if the concentration of microparticles in the sample is greater than the threshold value, determining that the platelets in a platelet product from which the sample was obtained are activated.

13. The method according to claim 12 wherein if the concentration of microparticles in the sample is equal to or less than the threshold value, determining that the platelets in a platelet product from which the sample was obtained are non-activated.

14. The method according to claim 11 in which the testing is performed using DLS and the activation indicators comprise microparticles.

15. A method of assessing platelets prior to transfusion of the platelets, comprising the steps of:
    a. using dynamic light scattering (DLS), screening an aliquot of platelets from a unit of platelets to determine the presence and content of activation indicators in the aliquot that correlate to the activation status of platelets in the aliquot, and wherein the activation indicators comprise microparticles;

b. if the content of activation indicators is equal to or less than a threshold value, allowing transfusion of the unit of platelets to a first patient group that comprises thrombocytopenic patients; and c. if the content of activation indicators exceeds the threshold value, prohibiting transfusion of the unit of platelets to the first patient group.

16. The method according to claim 15 in which the activation indicators comprise microparticles and the hydrodynamic radius of the microparticles is less than 1 micron.

17. The method according to claim 15 in which the first patient group comprises cancer patients.

18. The method according to claim 17 in which the cancer patients have a hematologic malignancy.

19. The method according to claim 16 including if the level of activation indicators exceeds the threshold value, allowing transfusion of the unit of platelets to a second patient group.

20. The method according to claim 19 including if the level of activation indicators is less than or equal to the threshold value, allowing transfusion of the unit of platelets to the first and second patient groups.

* * * * *